US012569419B2

(12) United States Patent
Bandera et al.

(10) Patent No.: US 12,569,419 B2
(45) Date of Patent: Mar. 10, 2026

(54) ANTIMICROBIAL COMPOSITION

(71) Applicant: Firmenich SA, Geneva (CH)

(72) Inventors: Monica Bandera, Geneva (CH); Nicholas O'leary, Paulsboro, NJ (US); Gary Marr, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 136 days.

(21) Appl. No.: 18/138,493

(22) Filed: Apr. 24, 2023

(65) Prior Publication Data

US 2023/0310288 A1 Oct. 5, 2023

Related U.S. Application Data

(63) Continuation of application No. 16/323,070, filed as application No. PCT/EP2017/069804 on Aug. 4, 2017, now Pat. No. 11,666,517.

(60) Provisional application No. 62/371,462, filed on Aug. 5, 2016.

(30) Foreign Application Priority Data

Aug. 31, 2016 (EP) .................................... 16186681

(51) Int. Cl.

| | |
|---|---|
| ***A61K 8/31*** | (2006.01) |
| ***A01N 31/02*** | (2006.01) |
| ***A01N 35/04*** | (2006.01) |
| ***A01N 43/08*** | (2006.01) |
| ***A61K 8/34*** | (2006.01) |
| ***A61K 8/35*** | (2006.01) |
| ***A61K 8/40*** | (2006.01) |
| ***A61K 8/41*** | (2006.01) |
| ***A61K 8/49*** | (2006.01) |
| ***A61Q 13/00*** | (2006.01) |
| ***A61Q 17/00*** | (2006.01) |
| *A61L 9/01* | (2006.01) |

(52) U.S. Cl.

CPC ................ *A61K 8/31* (2013.01); *A01N 31/02* (2013.01); *A01N 35/04* (2013.01); *A01N 43/08* (2013.01); *A61K 8/34* (2013.01); *A61K 8/342* (2013.01); *A61K 8/347* (2013.01); *A61K 8/35* (2013.01); *A61K 8/40* (2013.01); *A61K 8/41* (2013.01); *A61K 8/49* (2013.01); *A61K 8/4926* (2013.01); *A61K 8/4973* (2013.01); *A61Q 13/00* (2013.01); *A61Q 17/005* (2013.01); *A61K 2800/56* (2013.01); *A61K 2800/77* (2013.01); *A61L 9/01* (2013.01)

(58) Field of Classification Search

CPC . A61K 8/31; A61K 8/34; A61K 8/342; A61K 8/347; A61K 8/35; A61K 8/40; A61K 8/41; A61K 8/49; A61K 8/4926; A61K 8/4973; A61K 2800/56; A61K 2800/77; A61K 8/33; A61K 8/345; A01N 31/02; A01N 35/04; A01N 43/08; A01N 27/00; A01N 31/04; A01N 31/08; A01N 35/10; A01N 43/30; A01N 43/40; A61Q 13/00; A61Q 17/005; A61Q 19/10; A61L 9/01

See application file for complete search history.

(56) References Cited

U.S. PATENT DOCUMENTS

| | | | |
|---|---|---|---|
| 5,569,660 | A | 10/1996 | Snowden et al. |
| 2004/0059005 | A1 | 3/2004 | White |
| 2005/0049301 | A1 | 3/2005 | Bretler |
| 2012/0107258 | A1 | 5/2012 | Kuhn et al. |
| 2014/0315772 | A1 | 10/2014 | Cunningham |
| 2014/0350121 | A1 | 11/2014 | Commell |
| 2015/0051297 | A1 | 2/2015 | Commell |

FOREIGN PATENT DOCUMENTS

| | | | |
|---|---|---|---|
| JP | H09169624 | A | 6/1997 |
| KR | 20030068799 | A | 8/2003 |
| WO | WO 2004/073669 | * | 9/2004 |

OTHER PUBLICATIONS

Pilevar et al. J Pharm Nutr Sci. 2013; 3: 270-283. (Year: 2013).*
International Search Report and Written Opinion for PCT Application No. PCT/EP2017/069804, dated Apr. 25, 2018.
Malek, B., et al. Chemical composition and antimicrobial activity of essential oils from Scabiosa arenaria Forssk: growing wild in Tunisia, Chemistry & Biodiversity, vol. 9, No. 4, p. 831-832, 2012.
Matthew, J. et al., Chemical composition and antimicrobial activity of the leaf oil Amomum cannicarpum (Wight) Bentham ex Baker, The Journal of Essential Oil Research, vol. 18, No. 1, p. 35-37. 2006.
Deepak, C. et al., Essential oil composition of acorus calamus from district-pithoragarh, Uttarakhand, India. World Journal of Pharmaceutical Research, vol. 4, No. 9, p. 1158-1166, 2015.

(Continued)

*Primary Examiner* — David Browe

(74) *Attorney, Agent, or Firm* — Armstrong Teasdale LLP

(57) ABSTRACT

The present disclosure relates to the field of antimicrobial compositions. More particularly, it concerns the use of a composition as an antimicrobial agent, the composition comprising ingredients selected from the group consisting of: (i) nona-2,6-dien-1-ol in combination with at least one ingredient selected from the group consisting of 3-neopentylpyridine, 2-methylhexan-3-one oxime, terpineol and 2-isopropyl-5-methylphenol; (ii) gamma-dodecalactone in combination with at least one ingredient selected from the group consisting of 1-Methyl-4-(1-methylethenyl)-cyclohexene, 4-Methoxybenzaldehyde, and 1,3-Benzodioxole-5-carbaldehyde; (iii) (Z)-3,7-Dimethyl-2,6-octadien-1-ol and gamma-dodecalactone; (iv) cis-4(Isopropyl)cyclohexanemethanol and 4-Methoxybenzaldehyde; and (v) 1,3-Benzodioxole-5-carbaldehyde and 4-Methoxybenzaldehyde, wherein the ingredients are present in an amount sufficient to provide an antimicrobial effect. The composition and its use for the preparation of antimicrobially active perfuming compositions and consumer products are also objects of the disclosure.

15 Claims, No Drawings

(56) References Cited

OTHER PUBLICATIONS

Pietro, C., et al. Essential oils composition of two Sicilian cultivars of *Opuntia ficus-indica* (L.) Mill. (Cactaceae) fruits (prickly pear), Natural Product Research, vol. 27, No. 14, p. 1305-1314, 2013.
Unknown author; tilte: 2,6-nonadien-1-ol, product information downloaded from http://www.thegoodscentscompany.com/data/ rw 1383231.html (Year: 2021).
Adams et al: title: The FEMA GRAS assessment of a , b-unsaturated aldehydes and related substances uses as a flavor ingredients; Food Chemical Toxicology, vol. 46, 2008, pp. 2935-2967. (Year: 2008).
Api et al, title: RIFM fragrance ingredient safety assessment, (2E,6Z)-Nona-2,6-eien1-ol, CAS registry No. 28069-72-9, Food and Chemical Toxicology, vol. 84, pp. 557-565, published online Jul. 2, 2015 (Year: 2015).
Pubchem, title: ((2E,6Z)-Nona-2,6-eien1-ol, created Mar. 27, 2005. (Year: 2005).
Essential oils composition of two Sicilian cultivars of *Opuntia ficus-indica* (L.) Mill. (Cactaceae) fruits (prickly pear) dated Nov. 21, 2012; Table S1. Biological role described for some essential oils components of the fruits arranged by class; P. Zito, M. Sajeva, M. Bruno, S. Rosselli, A. Maggio, F. Senatore; 2 pages.
Essential oils composition of two Sicilian cultivars of *Opuntia ficus-indica* (L.) Mill. (Cactaceae) fruits (prickly pear) dated Nov. 21, 2012; Table S2. Fresh weight used from the fresh matrices with the yielded quantities and percent (w/w); P. Zito, M. Sajeva, M. Bruno, S. Rosselli, A. Maggio, F. Senatore; 1 page.
Deans et al., "Antibacterial activity of French tarragon (*Artemisia dracunculus* Linn.) essential oil and its constituents during ontogeny", Journal of Horticultural Science, 1988, pp. 503-508, 63(3).
Knobloch et al., "Antibacterial and Antifungal Properties of Essential Oil Components", Journal of Essential Oil Research, 1989, pp. 119-128, 1(3).
Aridoğan et al., "Antimicrobial Activity and Chemical Composition of Some Essential Oils", Archives of Pharmacal Research, 2002, pp. 860-864, 25(6).
Czerny et al., "Odor-Active Compounds in Cardboard", Journal of Agricultural and Food Chemistry, 2009, pp. 9979-9984, 57(21).
Paschke et al., "Toward the stereochemical identification of prohibited characterizing flavors in tobacco products: the case of strawberry flavor", Archives of Toxicology, 2015, pp. 1241-1255, 89(8).

* cited by examiner

ANTIMICROBIAL COMPOSITION

CROSS REFERENCE TO RELATED APPLICATIONS

This application is a continuation of application Ser. No. 16/323,070, filed on Feb. 4, 2019, which is the U.S. National Phase Application of PCT Application No. PCT/EP2017/069804, filed on Aug. 4, 2017, which claims priority to U.S. Provisional Patent Application Ser. No. 62/371,462, filed on Aug. 5, 2016, and European Patent Application Serial No. 16186681.9, filed on Aug. 31, 2016, the entire contents of which are incorporated by reference in their entirety.

TECHNICAL FIELD

The present disclosure relates to the field of antimicrobial compositions and their use as antibacterial agents, or their use for the preparation of antimicrobially active perfuming compositions and consumer products. More particularly, the present disclosure relates to compositions selected from the group consisting of: (i) nona-2,6-dien-1-ol in combination with at least one ingredient selected from the group consisting of 3-neopentylpyridine, 2-methylhexan-3-one oxime, terpineol and 2-isopropyl-5-methylphenol; (ii) gamma-dodecalactonein combination with at least one ingredient selected from the group consisting of 1-Methyl-4-(1-methylethenyl)-cyclohexene, 4-Methoxybenzaldehyde, and 1,3-Benzodioxole-5-carbaldehyde; (iii) (Z)-3,7-Dimethyl-2,6-octadien-1-ol and gamma-dodecalactone; (iv) cis-4(Isopropyl)cyclohexanemethanol and 4-Methoxybenzaldehyde; and (v) 1,3-Benzodioxole-5-carbaldehyde and 4-Methoxybenzaldehyde, wherein the ingredients are present in an amount sufficient to provide an antimicrobial effect, wherein the antimicrobial effect is an inhibition of growth of a bacterial strain selected from the group consisting of: *S. aureus* and *E. coli*.

BACKGROUND

Hygiene is a vast subject, which in its fullest meaning goes beyond simple 'cleanliness' to include, in addition to products, processes and devices, all circumstances and practices, lifestyle habits and premises that engender and foster a safe and healthy environment. In particular, hygiene refers to conditions and practices that help to maintain health and prevent the spread of diseases and therefore includes a specific set of practices associated with this preservation of health, for example environmental cleaning, sterilization of equipment, hand hygiene, water and sanitation or safe disposal of medical waste.

To improve hygiene, compounds having antimicrobial effects have been developed. However, the most currently used biocides such as Triclocarban and Triclosan are questioned by consumer or/and authorities, as such products are suspected to be endocrine disrupters. Consequently, there is a need to find antimicrobial ingredients having no or lower side effects, while maintaining a good antimicrobial activity.

In one example, U.S. Pat. No. 7,759,058 discloses an antimicrobial composition containing at least 30% by weight of one or more perfuming ingredients including nona-2,6-dien-1-ol.

In another example, International Patent Application Publication No. WO2005079573 reports a fragrance composition providing, as expected, an organoleptic effect but also an antifungal activity in a vapor phase. The antifungal composition comprises at least 50% by weight of the total composition of at least two perfuming ingredients selected from several lists of ingredients comprising among others 2,6-nonadienol and thymol. However, according to those teachings, a large amount of perfuming ingredients is required to deliver antimicrobial properties, which strongly influences the odor profile of the end-product containing those compositions, therefore limiting their use as an antimicrobial agent.

In another example, U.S. Pat. No. 9,339,477 discloses an antimicrobial composition for personal cleaning, oral care or hard surface cleaning applications. Wherein, it was found that compositions comprising thymol, selected propen-2-yl-methyl-cyclohexanols, and a carrier provide synergistic antimicrobial action.

In another example, U.S. Pat. No. 5,453,276 discloses antimicrobial compositions for controlling *P. aeruginosa* or *P. acnes* which contains indole and a naturally occurring substance selected from the group consisting of anacardic acid, limonene, beta-pinene, farnesol, beta-citronellol, pine resin, hinokitiol, longifolene, and beta-caryophyllene.

However, despite the availability of antimicrobial compounds and compositions, there remains a continuous need to find alternative antimicrobial compositions and active compounds that are suitable for use in such compositions. Without intending to be limited to any particular theory, the availability of alternatives may reduce the risk of development of microbial resistance and/or insensitivity to particular antimicrobial compounds.

Therefore, there is still a need to provide compositions having an antimicrobial effect, comprising ingredients having a minor impact on the overall perfume profile of the product in which the composition is added while maintaining or even improving the efficacy of the compositions in order to shorter contact time required for effective antimicrobial action.

The present disclosure provides a solution to the above mentioned problem by using as an antimicrobial agent, compositions selected from the group consisting of: (i) nona-2,6-dien-1-ol in combination with at least one ingredient selected from the group consisting of 3-neopentylpyridine, 2-methylhexan-3-one oxime, terpineol and 2-isopropyl-5-methylphenol; (ii) gamma-dodecalactone in combination with at least one ingredient selected from the group consisting of 1-Methyl-4-(1-methylethenyl)-cyclohexene, 4-Methoxybenzaldehyde, and 1,3-Benzodioxole-5-carbaldehyde; (iii) (Z)-3,7-Dimethyl-2,6-octadien-1-ol and gamma-dodecalactone; (iv) cis-4(Isopropyl)cyclohexanemethanol and 4-Methoxybenzaldehyde; and (v) 1,3-Benzodioxole-5-carbaldehyde and 4-Methoxybenzaldehyde, wherein the ingredients are present in an amount sufficient to provide an antimicrobial effect, wherein the antimicrobial effect is an inhibition of growth of a bacterial strain selected from the group consisting of: *S. aureus* and *E. coli*. The compositions of the present disclosure can advantageously be used at low concentrations while a significant antimicrobial effect is surprisingly observed. The use has not been disclosed or suggested heretofore.

SUMMARY

In one aspect, the present disclosure provides a composition comprising ingredients selected from the group consisting of: (i) nona-2,6-dien-1-ol in combination with at least one ingredient selected from the group consisting of 3-neopentylpyridine, 2-methylhexan-3-one oxime, terpineol and 2-isopropyl-5-methylphenol; (ii) gamma-dodecalactone in combination with at least one ingredient selected from the group consisting of 1-Methyl-4-(1-methylethenyl)-cyclohexene, 4-Methoxybenzaldehyde, and 1,3-Benzodioxole-5-carbaldehyde; (iii) (Z)-3,7-Dimethyl-2,6-octadien-1-ol and gamma-dodecalactone; (iv) cis-4(Isopropyl)cyclohexanemethanol and 4-Methoxybenzaldehyde; and (v) 1,3-Benzodioxole-5-carbaldehyde and 4-Methoxybenzaldehyde, wherein the ingredients are present in an amount sufficient to provide an antimicrobial effect.

In one aspect, the composition provides the antimicrobial effect by inhibiting the growth of bacteria. In one aspect, the antimicrobial effect is an inhibition of growth of a bacterial strain selected from the group consisting of: *C. xerosis, S. aureus* and *E. coli.*

In one aspect, the present invention provides a method, comprising treating a substrate comprising microbes with a composition according to some aspects of the present disclosure, in an amount effective to provide an antimicrobial effect.

In one aspect, the composition comprises nona-2,6-dien-1-ol and at least one compound selected from the group consisting of 3-neopentylpyridine, terpineol, and 2-methylhexan-3-one oxime. In one aspect, the amount sufficient of the nona-2,6-dien-1-ol is from 75 to 300 ppm, the amount sufficient of the 3-neopentylpyridine is from 75 to 150 ppm, the amount sufficient of the terpineol is from 300 to 600 ppm, and the amount sufficient of the 2-methylhexan-3-one oxime is from 1000 to 1200 ppm.

In one aspect, the composition comprises nona-2,6-dien-1-ol and at least one compound selected from the group consisting of 2-isopropyl-5-methylphenol, and 3-neopentylpyridine. In one aspect, the amount sufficient of the nona-2,6-dien-1-ol is from 75 to 300 ppm, the amount sufficient of the 2-isopropyl-5-methylphenol is from 100 to 200 ppm, and the amount sufficient of the 3-neopentylpyridine is from 75 to 150 ppm.

In one aspect, the composition comprises gamma-dodecalactone and at least one compound selected from the group consisting of 4-Methoxybenzaldehyde, and 1,3-Benzodioxole-5-carbaldehyde. In one aspect, the amount sufficient of the gamma-dodecalactone is from 150 to 600 ppm, the amount sufficient of the 4-Methoxybenzaldehyde is from 300 to 600 ppm, and the amount sufficient of the 1,3-Benzodioxole-5-carbaldehyde is from 300 to 600 ppm.

In one aspect, the composition comprises (Z)-3,7-Dimethyl-2,6-octadien-1-ol and gamma-dodecalactone. In one aspect, the amount sufficient of the (Z)-3,7-Dimethyl-2,6-octadien-1-ol is from 150 to 300 ppm, and the amount sufficient of the gamma-dodecalactone is from 150 to 600 ppm.

In one aspect, the composition comprises cis-4(Isopropyl) cyclohexanemethanol and 4-Methoxybenzaldehyde. In one aspect, the amount sufficient of the cis-4(Isopropyl)cyclohexanemethanol is from 600 to 2400 ppm, and the amount sufficient of the 4-Methoxybenzaldehyde is from 150 to 300 ppm.

In one aspect, the composition comprises 1,3-Benzodioxole-5-carbaldehyde and 4-Methoxybenzaldehyde. In one aspect, the amount sufficient of the 1,3-Benzodioxole-5-carbaldehyde is from 75 to 300 ppm, and the amount sufficient of the 4-Methoxybenzaldehyde is from 150 to 300 ppm.

In one aspect, the composition further comprises at least one ingredient selected from the group consisting of a perfumery carrier, a perfuming co-ingredient and mixtures thereof, and optionally at least one perfumery adjuvant.

In one aspect, the composition is formulated as a consumer product, wherein the consumer product is a perfume, a fabric care product, a body-care product, a cosmetic preparation, a skin-care product, an air care product or a home care product. In one aspect, the consumer product is a fine perfume, a splash or eau de perfume, a cologne, an shave or after-shave lotion, a liquid or solid detergent, a fabric softener, a fabric refresher, an ironing water, a paper, a bleach, a carpet cleaners, curtain-care products a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a “ready to use” powdered air freshener, a mold remover, furnisher care, wipe, a dish detergent or hard-surface detergent, a leather care product, a car care product.

DESCRIPTION OF THE INVENTION

In some aspects, the present disclosure provides a composition comprising ingredients selected from the group consisting of: (i) nona-2,6-dien-1-ol in combination with at least one ingredient selected from the group consisting of 3-neopentylpyridine, 2-methylhexan-3-one oxime, terpineol and 2-isopropyl-5-methylphenol; (ii) gamma-dodecalactone in combination with at least one ingredient selected from the group consisting of 1-Methyl-4-(1-methylethenyl)-cyclohexene, 4-Methoxybenzaldehyde, and 1,3-Benzodioxole-5-carbaldehyde; (iii) (Z)-3,7-Dimethyl-2,6-octadien-1-ol and gamma-dodecalactone; (iv) cis-4(Isopropyl)cyclohexanemethanol and 4-Methoxybenzaldehyde; and (v) 1,3-Benzodioxole-5-carbaldehyde and 4-Methoxybenzaldehyde, wherein the ingredients are present in an amount sufficient to provide an antimicrobial effect. In some aspects, the antimicrobial effect is unexpected.

In some aspects, the composition provides the antimicrobial effect by inhibiting the growth of bacteria. In one aspect, the antimicrobial effect is an inhibition of growth of a bacterial strain selected from the group consisting of: *C. xerosis, S. aureus* and *E. coli.*

In some aspects, the individual ingredients themselves possess an antimicrobial activity; however, the amount sufficient to provide the antimicrobial effect for the individual ingredient when combined in the composition is less than the amount sufficient to provide the antimicrobial effect of a given individual ingredient used separately.

In some aspects, the amount sufficient to provide an antimicrobial effect has no impact on the overall odour profile of the composition.

In some aspects, the composition of the present disclosure, or the use thereof, enables the amount of other bioactive ingredients such as, for example, triclosan, to be reduced, without impacting the overall perfume profile as the antimicrobial effect of the composition is obtained at low dosages.

In some aspects, the present disclosure provides a use, or a method of use of a composition comprising ingredients selected from the group consisting of: (i) nona-2,6-dien-1-ol in combination with at least one ingredient selected from the group consisting of 3-neopentylpyridine, 2-methylhexan-3-one oxime, terpineol and 2-isopropyl-5-methylphenol; (ii) gamma-dodecalactone in combination with at least one ingredient selected from the group consisting of 1-Methyl-4-(1-methylethenyl)-cyclohexene, 4-Methoxybenzaldehyde, and 1,3-Benzodioxole-5-carbaldehyde; (iii) (Z)-3,7-Dimethyl-2,6-octadien-1-ol and gamma-dodecalactone; (iv)

cis-4(Isopropyl)cyclohexanemethanol and 4-Methoxybenzaldehyde; and (v) 1,3-Benzodioxole-5-carbaldehyde and 4-Methoxybenzaldehyde, wherein the ingredients are present in an amount sufficient to provide an antimicrobial effect.

By "terpineol", it is meant the normal meaning in the art; i.e. α-terpineol, β-terpineol, γ-terpineol, terpinen-4-ol or mixture thereof. Alternatively the terpineol presents in the composition is α-terpineol or terpinen-4-ol. Alternatively, terpineol presents in the composition is α-terpineol. In some aspects, the compound has the following structure:

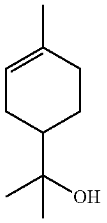

Nona-2,6-dien-1-ol may be in a form of any one of its stereoisomers or a mixture thereof. Nona-2,6-dien-1-ol has two carbon-carbon double bonds. Each carbon-carbon double bond of the compound, independently from each other, can be in a configuration Z or E or a mixture thereof. For the sake of clarity, by the expression "each carbon-carbon double bond of the compound, independently from each other, can be in a configuration Z or E or a mixture thereof" it is meant also a composition of matter comprising the various (E,E), (E,Z), (Z,E) and (Z,Z) isomers of nona-2,6-dien-1-ol. Alternatively, (2E,6Z)-nona-2,6-dien-1-ol is used. In some aspects, nona-2,6-dien-1-ol has the following structure:

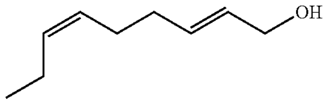

The ingredient 2-isopropyl-5-methylphenol is also known under the name Thymol, or the compound having the following structure:

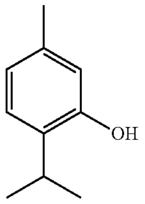

The ingredient 2-methylhexan-3-one oxime is also known as vertoxime, or the compound having the structure:

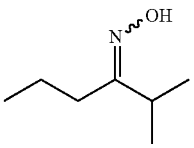

The ingredient 3-neopentylpyridine is also known as fructopyridine, or the compound having the structure:

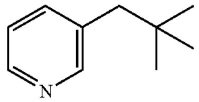

The ingredient 2-isopropyl-5-metylpolyphenol is also known as limonene, or decomposed Portugal.

The ingredient 4-methoxybenzaldehyde is also known as anisic aldeyhde, or the compound having the structure:

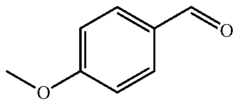

The ingredient 1,3-benzodioxole-5-carbaldehyde is also known as heliotropine, or the compound having the structure:

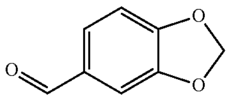 [SMILES: O=Cc1ccc2c(c1)OCO2]

The ingredient (Z)-3,7-dimethyl-2,6-octadien-1-ol is also known as geraniol, or the compound having the structure:

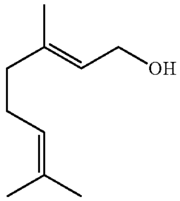

The ingredient cis-4(isopropyl)cyclohexanemethanol is also known as mayol, or the compound having the structure:

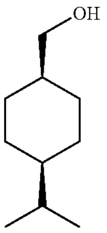

The ingredient gamma-dodecalactone is also known as decal, or the compound having the structure:

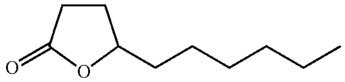

According to any one of the above aspects, the composition is used as an antibacterial agent. A non-limiting list of bacteria for which the composition are particularly effective includes *Escherichia coli*, DSMZ 1103 (origin: DSMZ—Deutsche Sammlung von Mikroorganismen und Zellkulturen GmbH) or *Staphylococcus aureus*, DSMZ 1104 (origin: DSMZ—Deutsche Sammlung von Mikroorganismen und Zellkulturen GmbH), or *Corynebacterium* xerosis, ATCC 373 (origin: ATCC—American Type Culture Collection).

By the term "antimicrobial agent", it is meant the normal meaning in the art; i.e. an agent which kills microorganism or inhibits their growth.

In some aspects, the present disclosure provides an antimicrobial composition comprising nona-2,6-dien-1-ol and at least one compound selected from the group consisting of 3-neopentylpyridine, terpineol, and 2-methylhexan-3-one oxime. Alternatively, in some aspects, the present disclosure provides the use of a composition comprising nona-2,6-dien-1-ol and at least one compound selected from the group consisting of 3-neopentylpyridine, terpineol, and 2-methylhexan-3-one oxime as an antimicrobial agent.

In some aspects, the present disclosure provides an antimicrobial composition comprising nona-2,6-dien-1-ol and at least one compound selected from the group consisting of 2-isopropyl-5-methylphenol, and 3-neopentylpyridine. Alternatively, in some aspects, the present disclosure provides the use of a composition comprising nona-2,6-dien-1-ol and at least one compound selected from the group consisting of 2-isopropyl-5-methylphenol, and 3-neopentylpyridine as an antimicrobial agent.

In some aspects, the present disclosure provides an antimicrobial composition comprising gamma-dodecalactone and at least one compound selected from the group consisting of 4-Methoxybenzaldehyde, and 1,3-Benzodioxole-5-carbaldehyde. Alternatively, in some aspects, the present disclosure provides the use of a composition comprising gamma-dodecalactone and at least one compound selected from the group consisting of 4-Methoxybenzaldehyde, and 1,3-Benzodioxole-5-carbaldehyde as an antimicrobial agent.

In some aspects, the present disclosure provides an antimicrobial composition comprising gamma-dodecalactone and 1-Methyl-4-(1-methylethenyl)-cyclohexene. Alternatively, in some aspects, the present disclosure provides the use of a composition comprising gamma-dodecalactone and 1-Methyl-4-(1-methylethenyl)-cyclohexene as an antimicrobial agent.

In some aspects, the present disclosure provides an antimicrobial composition comprising (Z)-3,7-Dimethyl-2,6-octadien-1-ol and gamma-dodecalactone. Alternatively, in some aspects, the present disclosure provides the use of a composition comprising (Z)-3,7-Dimethyl-2,6-octadien-1-ol and gamma-dodecalactone as an antimicrobial agent.

In some aspects, the present disclosure provides an antimicrobial composition comprising cis-4(Isopropyl)cyclohexanemethanol and 4-Methoxybenzaldehyde. Alternatively, in some aspects, the present disclosure provides the use of a composition comprising cis-4(Isopropyl)cyclohexanemethanol and 4-Methoxybenzaldehyde as an antimicrobial agent.

In some aspects, the present disclosure provides an antimicrobial composition comprising 1,3-Benzodioxole-5-carbaldehyde and 4-Methoxybenzaldehyde. Alternatively, in some aspects, the present disclosure provides the use of a composition comprising 1,3-Benzodioxole-5-carbaldehyde and 4-Methoxybenzaldehyde as an antimicrobial agent.

In some aspects, the composition used in the present disclosure comprises nona-2,6-dien-1-ol in an amount above 25 ppm, alternatively in an amount between 25 ppm and 2000 ppm, alternatively in an amount between 50 ppm and 1500 ppm. Alternatively, the composition comprises nona-2,6-dien-1-ol in an amount between 50 ppm and 800 ppm; or in an amount between 200 ppm and 1500 ppm. Alternatively the composition comprises nona-2,6-dien-1-ol in an amount between 50 ppm and 500 ppm, alternatively in an amount between 50 ppm and 200 ppm. Alternatively, the composition comprises 75 ppm, 150 ppm, 300 ppm or 600 ppm of nona-2,6-dien-1-ol.

In some aspects, the composition used in the present disclosure comprises nona-2,6-dien-1-ol and 3-neopentylpyridine. In some aspects, the composition comprises at least 25 ppm, alternatively at least 75 ppm of nona-2,6-dien-1-ol and at least 25 ppm, alternatively at least 75 ppm of 3-neopentylpyridine. Alternatively, the composition comprises nona-2,6-dien-1-ol in an amount between 25 and 450 ppm, alternatively between 75 and 300 ppm and alternatively between 75 and 150 ppm and 3-neopentylpyridine in an amount between 25 and 450 ppm, alternatively 75 and 300 ppm and alternatively between 75 and 150 ppm. Alternatively the composition comprises nona-2,6-dien-1-ol in an amount between 25 and 250 ppm, alternatively between 50 and 200 ppm and alternatively between 75 and 150 ppm and 3-neopentylpyridine in an amount between 25 and 125 ppm, alternatively between 50 and 100 ppm and alternatively between 65 and 85 ppm; or the composition comprises nona-2,6-dien-1-ol in an amount between 25 and 125 ppm, alternatively between 50 and 100 ppm and alternatively between 65 and 85 ppm and 3-neopentylpyridine in an amount between 25 and 250 ppm, alternatively between 50 and 200 ppm and alternatively between 75 and 150 ppm. Alternatively the composition comprises (2E,6Z)-nona-2,6-dien-1-ol in an amount between 75 and 150 ppm and 75 ppm of 3-neopentylpyridine; or the composition comprises 75 ppm of (2E,6Z)-nona-2,6-dien-1-ol and 3-neopentylpyridine in an amount between 75 and 150 ppm.

In some aspects, the composition used in the present disclosure comprises nona-2,6-dien-1-ol and 2-methylhexan-3-one oxime. In some aspects, the composition comprises at least 400 ppm, alternatively at least 600 ppm of nona-2,6-dien-1-ol and at least 100 ppm, alternatively at least 150 ppm of methylhexan-3-one oxime; or at least 200 ppm, alternatively at least 300 ppm of nona-2,6-dien-1-ol and at least 700 ppm, alternatively at least 1200 ppm of methylhexan-3-one oxime; or at least 25 ppm, alternatively at least 75 ppm of nona-2,6-dien-1-ol and at least 1800 ppm, alternatively at least 2400 ppm of methylhexan-3-one oxime. Alternatively, the composition comprises nona-2,6-dien-1-ol in an amount between 25 and 225 ppm and alternatively between 75 and 150 ppm and 2-methylhexan-3-one oxime in an amount between 1800 and 3600 ppm and alternatively between 2100 and 2700 ppm; or nona-2,6-dien-1-ol in an amount between 400 and 1000 ppm, alternatively between 500 and 800 ppm and alternatively between 550 and 650 ppm and 2-methylhexan-3-one oxime in an amount between 100 and 800 ppm and alternatively between 150 and 600 ppm; or nona-2,6-dien-1-ol in an amount between 200 and 500 ppm, alternatively between 250 and 450 ppm and alternatively between 250 and 350 ppm and 2-methylhexan-3-one oxime in an amount between 700 and 2000 ppm, alternatively between 800 and 1600 ppm, and alternatively between 1000 and 1400 ppm. Alternatively, the composition comprises 300 ppm of nona-2,6-dien-1-ol and 1200 ppm of 2-methylhexan-3-one oxime.

In some aspects, the composition used in the present disclosure comprises nona-2,6-dien-1-ol and terpineol. In some aspects, the composition comprises at least 200 ppm, alternatively at least 300 ppm of nona-2,6-dien-1-ol and at least 400 ppm, alternatively at least 600 ppm of terpineol; or at least 400 ppm, alternatively at least 600 ppm of nona-2,6-dien-1-ol and at least 200 ppm, alternatively at least 300 ppm of terpineol; or at least 700 ppm, alternatively at least 1200 ppm of nona-2,6-dien-1-ol and at least 25 ppm, alternatively at least 75 ppm of terpineol. Alternatively, the composition comprises nona-2,6-dien-1-ol in an amount between 200 and 400 ppm and alternatively between 250 and 350 ppm and terpineol in an amount between 400 and 1000 ppm, alternatively between 500 and 800 ppm and alternatively between 550 and 650 ppm; or nona-2,6-dien-1-ol in an amount between 700 and 2000 ppm, alternatively between 800 and 1600 ppm, and alternatively between 1000 and 1400 ppm and terpineol in an amount between 25 and 250 ppm and alternatively between 75 and 150 ppm; or nona-2,6-dien-1-ol in an amount between 400 and 1000 ppm, alternatively between 500 and 800 ppm and alternatively between 550 and 650 ppm and terpineol in an amount between 200 and 500 ppm, alternatively between 250 and 450 ppm and alternatively between 250 and 350 ppm. Alternatively, the composition comprises 600 ppm of nona-2,6-dien-1-ol and 300 ppm of terpineol.

In some aspects, the composition used in the present disclosure comprises nona-2,6-dien-1-ol and 2-isopropyl-5-methylphenol. In some aspects, the composition comprises at least 25 ppm, alternatively at least 75 ppm of nona-2,6-dien-1-ol and at least 200 ppm, alternatively at least 300 ppm of 2-isopropyl-5-methylphenol; or at least 100 ppm, alternatively at least 150 ppm of nona-2,6-dien-1-ol and at least 100 ppm, alternatively at least 150 ppm of 2-isopropyl-5-methylphenol. Alternatively, the composition comprises nona-2,6-dien-1-ol in an amount between 25 and 125 ppm and alternatively between 50 and 100 ppm and 2-isopropyl-5-methylphenol in an amount between 200 and 500 ppm, alternatively between 250 and 450 ppm and alternatively between 250 and 350 ppm; or nona-2,6-dien-1-ol in an amount between 100 and 400 ppm, alternatively between 150 and 300 ppm and alternatively between 130 and 170 ppm and 2-isopropyl-5-methylphenol in an amount between 100 and 225 ppm and alternatively between 130 and 170 ppm. Alternatively, the composition comprises 150 ppm of nona-2,6-dien-1-ol and 150 ppm of 2-isopropyl-5-methylphenol.

In some aspects, the composition used in the present disclosure comprises gamma-dodecalactone in an amount above 25 ppm, alternatively in an amount between 25 ppm and 2000 ppm, alternatively in an amount between 50 ppm and 1500 ppm. Alternatively, the composition comprises gamma-dodecalactone in an amount between 50 ppm and 800 ppm; or in an amount between 200 ppm and 1500 ppm. Alternatively the composition comprises gamma-dodecalactone in an amount between 50 ppm and 500 ppm, alternatively in an amount between 50 ppm and 200 ppm. Alternatively, the composition comprises 75 ppm, 150 ppm, 300 ppm, 600 ppm, or 700 ppm of gamma-dodecalactone.

In some aspects, the composition used in the present disclosure comprises gamma-dodecalactone and 1-Methyl-4-(1-methylethenyl)-cyclohexene. In some aspects, the composition comprises at least 150 ppm, or, alternatively at least 200 ppm, alternatively at least 250 ppm, alternatively at least 300 ppm, alternatively at least 350 ppm, alternatively at least 400 ppm, alternatively at least 450 ppm, alternatively at least 500 ppm, alternatively at least 550 ppm, alternatively at least 600 ppm, alternatively at least 650 ppm, alternatively at least 700 ppm of gamma-dodecalactone and at least 150 ppm, or, alternatively at least 200 ppm, alternatively at least 250 ppm, alternatively at least 300 ppm, alternatively at least 350 ppm, alternatively at least 400 ppm, alternatively at least 450 ppm, or alternatively at least 500 ppm of 1-Methyl-4-(1-methylethenyl)-cyclohexene. Alternatively, the composition comprises gamma-dodecalactone in an amount between 200 and 700 ppm, alternatively between 200 and 600 ppm and alternatively between 300 and 600 ppm and 1-Methyl-4-(1-methylethenyl)-cyclohexene in an amount between 150 and 500 ppm, alternatively 150 and 500 ppm, alternatively 200 and 400 ppm, alternatively 250 and 400 ppm, and alternatively 300 and 400 ppm.

In some aspects, the composition comprises gamma-dodecalactone in an amount between 300 and 600 ppm and 300 ppm of 1-Methyl-4-(1-methylethenyl)-cyclohexene; or the composition comprises 300 ppm of gamma-dodecalactone and 1-Methyl-4-(1-methylethenyl)-cyclohexene in an amount between 200 and 400 ppm. Alternatively, the composition comprises 600 ppm of gamma-dodecalactone and 1-Methyl-4-(1-methylethenyl)-cyclohexene in an amount between 200 and 400 ppm.

In some aspects, the composition comprises 300 ppm of gamma-dodecalactone and 300 ppm 1-Methyl-4-(1-methylethenyl)-cyclohexene. In some aspects, the composition comprises 600 ppm of gamma-dodecalactone and 300 ppm 1-Methyl-4-(1-methylethenyl)-cyclohexene.

In some aspects, the composition used in the present disclosure comprises gamma-dodecalactone and 4-Methoxybenzaldehyde. In some aspects, the composition comprises at least 50 ppm, or alternatively at least 100 ppm, or alternatively at least 150 ppm, or alternatively at least 200 ppm, alternatively at least 250 ppm, alternatively at least 300 ppm, alternatively at least 350 ppm, alternatively at least 400 ppm, alternatively at least 450 ppm, alternatively at least 500 ppm, alternatively at least 550 ppm, alternatively at least 600 ppm, alternatively at least 650 ppm, alternatively at least 700 ppm of gamma-dodecalactone and at least 150 ppm, or, alternatively at least 200 ppm, alternatively at least 250 ppm, alternatively at least 300 ppm, alternatively at least 350 ppm, alternatively at least 400 ppm, alternatively at least 450 ppm, or alternatively at least 500 ppm of 4-Methoxybenzaldehyde. Alternatively, the composition comprises gamma-dodecalactone in an amount between 200 and 700 ppm, alternatively between 200 and 600 ppm and alternatively between 300 and 600 ppm and 4-Methoxybenzaldehyde in an amount between 50 and 500 ppm, alternatively 100 and 500 ppm, alternatively 150 and 400 ppm, alternatively 150 and 350 ppm, and alternatively 150 and 300 ppm.

In some aspects, the composition comprises gamma-dodecalactone in an amount between 300 and 600 ppm and 150 ppm of 4-Methoxybenzaldehyde; or the composition comprises 300 ppm of gamma-dodecalactone and 4-Methoxybenzaldehyde in an amount between 150 and 300 ppm. Alternatively, the composition comprises 600 ppm of gamma-dodecalactone and 4-Methoxybenzaldehyde in an amount between 150 and 300 ppm.

In some aspects, the composition comprises 300 ppm of gamma-dodecalactone and 150 ppm, or alternatively 200 ppm, alternatively 250 ppm, alternatively 300 ppm 4-Methoxybenzaldehyde. In some aspects, the composition comprises 600 ppm of gamma-dodecalactone and 150 ppm, or alternatively 200 ppm, alternatively 250 ppm, alternatively 300 ppm 4-Methoxybenzaldehyde.

In some aspects, the composition used in the present disclosure comprises gamma-dodecalactone and 1,3-Benzodioxole-5-carbaldehyde. In some aspects, the composition comprises at least 150 ppm, or, alternatively at least 200 ppm, alternatively at least 250 ppm, alternatively at least 300 ppm, alternatively at least 350 ppm, alternatively at least 400 ppm, alternatively at least 450 ppm, alternatively at least 500 ppm, alternatively at least 550 ppm, alternatively at least 600 ppm, alternatively at least 650 ppm, alternatively at least 700 ppm of gamma-dodecalactone and at least 150 ppm, or, alternatively at least 200 ppm, alternatively at least 250 ppm, alternatively at least 300 ppm, alternatively at least 350 ppm, alternatively at least 400 ppm, alternatively at least 450 ppm, alternatively at least 500 ppm, alternatively at least 550 ppm, alternatively at least 600 ppm, alternatively at least 650 ppm, or alternatively at least 700 ppm of 1,3-Benzodioxole-5-carbaldehyde. Alternatively, the composition comprises gamma-dodecalactone in an amount between 200 and 700 ppm, alternatively between 200 and 600 ppm and alternatively between 300 and 600 ppm and 1,3-Benzodioxole-5-carbaldehyde in an amount between 150 and 700 ppm, alternatively 150 and 600 ppm, alternatively 200 and 600 ppm, alternatively 250 and 600 ppm, and alternatively 300 and 600 ppm.

In some aspects, the composition comprises gamma-dodecalactone in an amount between 300 and 600 ppm and 600 ppm of 1,3-Benzodioxole-5-carbaldehyde; or the composition comprises 300 ppm of gamma-dodecalactone and 1,3-Benzodioxole-5-carbaldehyde in an amount between 300 and 600 ppm. Alternatively, the composition comprises 600 ppm of gamma-dodecalactone and 1,3-Benzodioxole-5-carbaldehyde in an amount between 300 and 600 ppm.

In some aspects, the composition comprises 300 ppm of gamma-dodecalactone and 300 ppm 1,3-Benzodioxole-5-carbaldehyde. In some aspects, the composition comprises 600 ppm of gamma-dodecalactone and 300 ppm 1,3-Benzodioxole-5-carbaldehyde. In some aspects, the composition comprises 300 ppm of gamma-dodecalactone and 600 ppm 1,3-Benzodioxole-5-carbaldehyde. In some aspects, the composition comprises 600 ppm of gamma-dodecalactone and 600 ppm 1,3-Benzodioxole-5-carbaldehyde.

In some aspects, the composition used in the present disclosure comprises (Z)-3,7-Dimethyl-2,6-octadien-1-ol in an amount above 25 ppm, alternatively in an amount between 25 ppm and 2000 ppm, alternatively in an amount between 50 ppm and 1500 ppm. Alternatively, the composition comprises (Z)-3,7-Dimethyl-2,6-octadien-1-ol in an amount between 50 ppm and 800 ppm; or in an amount between 200 ppm and 1500 ppm. Alternatively the composition comprises (Z)-3,7-Dimethyl-2,6-octadien-1-ol in an amount between 50 ppm and 500 ppm, alternatively in an amount between 50 ppm and 200 ppm. Alternatively, the composition comprises 75 ppm, 150 ppm, 300 ppm, 600 ppm, or 700 ppm of (Z)-3,7-Dimethyl-2,6-octadien-1-ol.

In some aspects, the composition used in the present disclosure comprises (Z)-3,7-Dimethyl-2,6-octadien-1-ol and gamma-dodecalactone. In some aspects, the composition comprises at least 50 ppm, or, alternatively at least 100 ppm, alternatively at least 150 ppm, alternatively at least 200 ppm, alternatively at least 250 ppm, alternatively at least 300 ppm, alternatively at least 350 ppm, or alternatively at least 400 ppm of (Z)-3,7-Dimethyl-2,6-octadien-1-ol and at least 150 ppm, or, alternatively at least 200 ppm, alternatively at least 250 ppm, alternatively at least 300 ppm, alternatively at least 350 ppm, alternatively at least 400 ppm, alternatively at least 450 ppm, or alternatively at least 500 ppm of gamma-dodecalactone. Alternatively, the composition comprises (Z)-3,7-Dimethyl-2,6-octadien-1-ol in an amount between 50 and 500 ppm, alternatively between 100 and 500 ppm and alternatively between 1500 and 5000 ppm and gamma-dodecalactone in an amount between 150 and 500 ppm, alternatively 150 and 500 ppm, alternatively 200 and 400 ppm, alternatively 250 and 400 ppm, and alternatively 300 and 400 ppm.

In some aspects, the composition comprises (Z)-3,7-Dimethyl-2,6-octadien-1-ol in an amount between 150 and 300 ppm and 300 ppm of gamma-dodecalactone; or the composition comprises 150 ppm of (Z)-3,7-Dimethyl-2,6-octadien-1-ol and gamma-dodecalactone in an amount between 200 and 400 ppm. Alternatively, the composition comprises 300 ppm of (Z)-3,7-Dimethyl-2,6-octadien-1-ol and gamma-dodecalactone in an amount between 200 and 400 ppm.

In some aspects, the composition used in the present disclosure comprises cis-4(Isopropyl)cyclohexanemethanol in an amount above 25 ppm, alternatively in an amount between 25 ppm and 4000 ppm, alternatively in an amount between 50 ppm and 1500 ppm. Alternatively, the composition comprises cis-4(Isopropyl)cyclohexanemethanol in an amount between 50 ppm and 800 ppm; or in an amount between 500 ppm and 3000 ppm. Alternatively the composition comprises cis-4(Isopropyl)cyclohexanemethanol in an amount between 300 ppm and 2500 ppm, alternatively in an amount between 600 ppm and 2400 ppm. Alternatively, the composition comprises 300 ppm, 400 ppm, 500 ppm, 600 ppm, 700 ppm, 800 ppm, 900 ppm, 1000 ppm, 1100 ppm, 1200 ppm, 1300 ppm, 1400 ppm, 1500 ppm, 1600 ppm, 1700 ppm, 1800 ppm, 1900 ppm, 2000 ppm, 2100 ppm, 2200 ppm, 2300 ppm, or 2400 ppm of cis-4(Isopropyl)cyclohexanemethanol.

In some aspects, the composition used in the present disclosure comprises cis-4(Isopropyl)cyclohexanemethanol and 4-Methoxybenzaldehyde. In some aspects, the composition comprises at least 300 ppm, 400 ppm, 500 ppm, 600 ppm, 700 ppm, 800 ppm, 900 ppm, 1000 ppm, 1100 ppm, 1200 ppm, 1300 ppm, 1400 ppm, 1500 ppm, 1600 ppm, 1700 ppm, 1800 ppm, 1900 ppm, 2000 ppm, 2100 ppm, 2200 ppm, 2300 ppm, or 2400 ppm of cis-4(Isopropyl)cyclohexanemethanol and at least 150 ppm, or, alternatively at least 200 ppm, alternatively at least 250 ppm, alternatively at least 300 ppm, alternatively at least 350 ppm, alternatively at least 400 ppm, alternatively at least 450 ppm, or alternatively at least 500 ppm of 4-Methoxybenzaldehyde. Alternatively, the composition comprises cis-4(Isopropyl)cyclohexanemethanol in an amount between 50 and 500 ppm, alternatively between 100 and 500 ppm and alternatively between 1500 and 5000 ppm and 4-Methoxybenzaldehyde in an amount between 150 and 500 ppm, alternatively 150 and 500 ppm, alternatively 200 and 400 ppm, alternatively 250 and 400 ppm, and alternatively 300 and 400 ppm.

In some aspects, the composition comprises cis-4(Isopropyl)cyclohexanemethanol in an amount between 600 and 2400 ppm and 300 ppm of 4-Methoxybenzaldehyde; or the composition comprises 600 ppm of cis-4(Isopropyl)cyclohexanemethanol and 4-Methoxybenzaldehyde in an amount between 150 and 300 ppm. Alternatively, the composition comprises 1200 ppm of cis-4(Isopropyl)cyclohexanemethanol and 4-Methoxybenzaldehyde in an amount between 150 and 300 ppm. Alternatively, the composition comprises 2400 ppm of cis-4(Isopropyl)cyclohexanemethanol and 4-Methoxybenzaldehyde in an amount between 150 and 300 ppm.

In some aspects, the composition used in the present disclosure comprises 1,3-Benzodioxole-5-carbaldehyde in an amount above 25 ppm, alternatively in an amount between 25 ppm and 2000 ppm, alternatively in an amount between 50 ppm and 1500 ppm. Alternatively, the composition comprises 1,3-Benzodioxole-5-carbaldehyde in an amount between 50 ppm and 800 ppm; or in an amount between 50 ppm and 3000 ppm. Alternatively the composition comprises 1,3-Benzodioxole-5-carbaldehyde in an amount between 25 ppm and 600 ppm, alternatively in an amount between 50 ppm and 600 ppm. Alternatively, the composition comprises 50 ppm, 60 ppm, 70 ppm, 80 ppm, 90 ppm, 100 ppm, 110 ppm, 120 ppm, 130 ppm, 140 ppm, 150 ppm, 160 ppm, 170 ppm, 180 ppm, 190 ppm, 200 ppm, 250 ppm, or 300 ppm of 1,3-Benzodioxole-5-carbaldehyde.

In some aspects, the composition used in the present disclosure comprises 1,3-Benzodioxole-5-carbaldehyde and 4-Methoxybenzaldehyde. In some aspects, the composition comprises at least 50 ppm, or, alternatively at least 100 ppm, alternatively at least 150 ppm, alternatively at least 200 ppm, alternatively at least 250 ppm, alternatively at least 300 ppm, alternatively at least 350 ppm, or alternatively at least 400 ppm of 1,3-Benzodioxole-5-carbaldehyde and at least 150 ppm, or, alternatively at least 200 ppm, alternatively at least 250 ppm, alternatively at least 300 ppm, alternatively at least 350 ppm, alternatively at least 400 ppm, alternatively at least 450 ppm, or alternatively at least 500 ppm of 4-Methoxybenzaldehyde. Alternatively, the composition comprises 1,3-Benzodioxole-5-carbaldehyde in an amount between 50 and 500 ppm, alternatively between 75 and 300 ppm and 4-Methoxybenzaldehyde in an amount between 150 and 500 ppm, alternatively 150 and 500 ppm, alternatively 200 and 400 ppm, alternatively 250 and 400 ppm, and alternatively 300 and 400 ppm.

In some aspects, the composition comprises 1,3-Benzodioxole-5-carbaldehyde in an amount between 75 and 300 ppm and 300 ppm of 4-Methoxybenzaldehyde; or the composition comprises 75 ppm of 1,3-Benzodioxole-5-carbaldehyde and 4-Methoxybenzaldehyde in an amount between 150 and 300 ppm. Alternatively, the composition comprises 300 ppm of 1,3-Benzodioxole-5-carbaldehyde and 4-Methoxybenzaldehyde in an amount between 150 and 300 ppm.

As shown in the examples below, the compositions presented herein demonstrate an antimicrobial effect. According to a particular aspect, the compositions even provide a synergistic antimicrobial effect; i.e. an effect which is superior to the simple sum or addition of the antimicrobial effect expected when the two ingredients of the composition would have been admixed in the desired concentration. In other words, in such cases, antibacterial activity of the combination of both ingredients is greater than the sum of activities of the individual ingredients. The synergistic effect may be determined firstly by measuring the Minimal Inhibitory Concentration (MIC) for each ingredient in isolation and in the combination. These MIC values can then be used to calculate the Fractional Inhibitory Index (FIC) for each agent and then the overall ΣFIC for the combination, as reported in Garcia L. S., Clinical Microbiology Procedures Handbook, pg. 140-162, 3rd Edition (2010), ASM Press, Washington DC. A composition is considered to have an additive antimicrobial effect also known as a partial antimicrobial synergistic effect when FIC Index in below 1. For FIC Index below 0.5, the composition is considered to have a synergistic antimicrobial effect.

The use of the compositions as defined here-in is particularly advantageous to limit or control the growth of microorganism such as bacteria. The antimicrobial effect is one of the main requirements of hygiene products such as body care or home care products.

As mentioned above, the disclosure concerns the use of the compositions as defined above as an antimicrobial agent.

In some aspects, the present disclosure provides a non-therapeutic method of affecting microbial activity, the method comprising treating a substrate comprising microbes with a composition comprising nona-2,6-dien-1-ol and at least one compound selected from the group consisting of 3-neopentylpyridine, 2-methylhexan-3-one oxime, terpineol and 2-isopropyl-5-methylphenol, wherein the substrate is treated with the composition in an amount sufficient to provide an antimicrobial effect.

In some aspects, the present disclosure provides a non-therapeutic method of affecting microbial activity, the method comprising treating a substrate comprising microbes with a composition comprising gamma-dodecalactone in combination with at least one ingredient selected from the group consisting of 1-Methyl-4-(1-methylethenyl)-cyclohexene, 4-Methoxybenzaldehyde, and 1,3-Benzodioxole-5-carbaldehyde, wherein the substrate is treated with the composition in an amount sufficient to provide an antimicrobial effect.

In some aspects, the present disclosure provides a non-therapeutic method of affecting microbial activity, the method comprising treating a substrate comprising microbes with a composition comprising 1,3-Benzodioxole-5-carbaldehyde and gamma-dodecalactone, wherein the substrate is treated with the composition in an amount sufficient to provide an antimicrobial effect.

In some aspects, the present disclosure provides a non-therapeutic method of affecting microbial activity, the method comprising treating a substrate comprising microbes with a composition comprising 1,3-Benzodioxole-5-carbaldehyde and 4-Methoxybenzaldehyde, wherein the composition is present in an amount sufficient to provide an antimicrobial effect.

In some aspects, the present disclosure provides a non-therapeutic method of affecting microbial activity, the method comprising treating a substrate comprising microbes with a composition comprising a composition comprising 1,3-Benzodioxole-5-carbaldehyde and 4-Methoxybenzaldehyde, wherein the composition is present in an amount sufficient to provide an antimicrobial effect.

By the term "affecting", it is meant the inhibition of growth of microorganisms or the killing of microorganisms.

In some aspects, the present disclosure provides an antimicrobial composition comprising nona-2,6-dien-1-ol and at least one compound selected from the group consisting of 3-neopentylpyridine, terpineol, and 2-methylhexan-3-one oxime.

In some aspects, the present disclosure provides an antimicrobial composition comprising nona-2,6-dien-1-ol and at least one compound selected from the group consisting of 2-isopropyl-5-methylphenol, and 3-neopentylpyridine.

In some aspects, the present disclosure provides an antimicrobial composition comprising gamma-dodecalactone and at least one compound selected from the group consisting of 4-Methoxybenzaldehyde, and 1,3-Benzodioxole-5-carbaldehyde.

In some aspects, the present disclosure provides an antimicrobial composition comprising gamma-dodecalactone and 1-Methyl-4-(1-methylethenyl)-cyclohexene.

In some aspects, the present disclosure provides an antimicrobial composition comprising 1,3-Benzodioxole-5-carbaldehyde and gamma-dodecalactone.

In some aspects, the present disclosure provides an antimicrobial composition comprising 1,3-Benzodioxole-5-carbaldehyde and 4-Methoxybenzaldehyde.

In some aspects, the present disclosure provides an antimicrobial composition comprising 1,3-Benzodioxole-5-carbaldehyde and 4-Methoxybenzaldehyde.

In some aspects, the present disclosure provides a perfuming composition comprising:

a) a composition comprising nona-2,6-dien-1-ol and a least one compound selected from the group consisting of 3-neopentylpyridine, 2-methylhexan-3-one oxime, terpineol and 2-isopropyl-5-methylphenol, wherein the composition is present in an amount sufficient to provide an antimicrobial effect;

b) at least one ingredient selected from the group consisting of a perfumery carrier, a perfuming co-ingredient and mixtures thereof; and c) optionally at least one perfumery adjuvant.

In some aspects, the present disclosure provides a perfuming composition comprising:

a) a composition comprising at least gamma-dodecalactone in combination with at least one ingredient selected from the group consisting of 1-Methyl-4-(1-methylethenyl)-cyclohexene, 4-Methoxybenzaldehyde, and 1,3-Benzodioxole-5-carbaldehyde, wherein the composition is present in an amount sufficient to provide an antimicrobial effect;

b) at least one ingredient selected from the group consisting of a perfumery carrier, a perfuming co-ingredient and mixtures thereof; and c) optionally at least one perfumery adjuvant.

In some aspects, the present disclosure provides a perfuming composition comprising: a) a composition comprising at least 1,3-Benzodioxole-5-carbaldehyde and gamma-dodecalactone, wherein the composition is present in an amount sufficient to provide an antimicrobial effect;

b) at least one ingredient selected from the group consisting of a perfumery carrier, a perfuming co-ingredient and mixtures thereof; and c) optionally at least one perfumery adjuvant.

In some aspects, the present disclosure provides a perfuming composition comprising:

a) a composition comprising at least cis-4(Isopropyl) cyclohexanemethanol and 4-Methoxybenzaldehyde, wherein the composition is present in an amount sufficient to provide an antimicrobial effect;

b) at least one ingredient selected from the group consisting of a perfumery carrier, a perfuming co-ingredient and mixtures thereof; and c) optionally at least one perfumery adjuvant.

In some aspects, the present disclosure provides a perfuming composition comprising:

a) a composition comprising at least 1,3-Benzodioxole-5-carbaldehyde and 4-Methoxybenzaldehyde, wherein the composition is present in an amount sufficient to provide an antimicrobial effect;

b) at least one ingredient selected from the group consisting of a perfumery carrier, a perfuming co-ingredient and mixtures thereof; and c) optionally at least one perfumery adjuvant.

In some aspects, the present disclosure provides a perfuming consumer product comprising a composition comprising nona-2,6-dien-1-ol and a least one compound selected from the group consisting of 3-neopentylpyridine, 2-methylhexan-3-one oxime, terpineol and 2-isopropyl-5-methylphenol, wherein the composition is present in an amount sufficient to provide an antimicrobial effect.

In some aspects, the present disclosure provides a perfuming consumer product comprising a composition comprising gamma-dodecalactone in combination with at least one ingredient selected from the group consisting of 1-Methyl-4-(1-methylethenyl)-cyclohexene, 4-Methoxybenzaldehyde, and 1,3-Benzodioxole-5-carbaldehyde, wherein the composition is present in an amount sufficient to provide an antimicrobial effect.

In some aspects, the present disclosure provides a perfuming consumer product comprising a composition comprising 1,3-Benzodioxole-5-carbaldehyde in combination and gamma-dodecalactone, wherein the composition is present in an amount sufficient to provide an antimicrobial effect.

In some aspects, the present disclosure provides a perfuming consumer product comprising a composition comprising cis-4(Isopropyl)cyclohexanemethanol and 4-Methoxybenzaldehyde, wherein the composition is present in an amount sufficient to provide an antimicrobial effect.

In some aspects, the present disclosure provides a perfuming consumer product comprising a composition comprising 1,3-Benzodioxole-5-carbaldehyde and 4-Methoxybenzaldehyde, wherein the composition is present in an amount sufficient to provide an antimicrobial effect.

The amounts of each ingredient in the antimicrobial composition are as defined above.

By "perfumery carrier" we mean here a material which is practically neutral from a perfumery point of view, i.e. which does not significantly alter the organoleptic properties of perfuming ingredients. The carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycols, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

As solid carrier it is meant a material where the perfuming composition or some element of the perfuming composition can be chemically or physically bound. In general such solid carrier are employed either to stabilize the composition, either to control the rate of evaporation of the compositions or of some ingredients. The employment of solid carrier is of current use in the art and a person skilled in the art knows how to reach the desired effect. However by way of non-limiting example as solid carriers one may cite absorbing gums or polymers or inorganic material, such as porous polymers, cyclodextrines, wood based materials, organic or inorganic gels, clays, gypsum talc or zeolites.

As other non-limiting example of solid carrier one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique. As non-limiting examples one may cite in particular the core-shell encapsulation with resins of the aminoplast, polyamide, polyester, polyurea or polyurethane type or a mixture thereof (all of the resins are well known to a person skilled in the art) using techniques like phase separation process induced by polymerization, by interfacial polymerization, by coacervation or altogether (all of the techniques are have been described in the prior art), and optionally in presence of polymeric stabilizer or a cationic copolymer.

In particular, as resins one may cite the ones produced by the polycondensation of an aldehyde (e.g. formaldehyde, 2,2-dimethoxyethanal, glyoxal, glyoxylic acid or glycolaldehyde and mixtures thereof) with an amine, namely urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

In particular, as resins one may cite the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate*, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins, with aldehydes is represented by articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors and creators have enriched the literature in this field and it would be impossible to cover all published developments here, but the general knowledge in this type of encapsulation is very significant. More recent publications of pertinence, which also address the suitable uses of such microcapsules, are represented for example by the article of H. Y. Lee et al. in Journal of Microencapsulation, 2002, vol. 19, pages 559-569, international patent publication WO 01/41915 or yet the article of S. Böne et al. in Chimia, 2011, vol. 65, pages 177-181.

Perfuming co-ingredients, when present in the perfuming composition, are other than nona-2,6-dien-1-ol, 3-neopentylpyridine, 2-methylhexan-3-one oxime, terpineol or 2-isopropyl-5-methylphenol. Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and the perfuming co-ingredients can be of natural or synthetic origin.

In particular one may cite perfuming co-ingredients which are commonly used in perfume formulations, such as:

- Aldehydic ingredients: decanal, dodecanal, 2-methyl-undecanal, 10-undecenal, octanal and/or nonenal;
- Aromatic-herbal ingredients: *eucalyptus* oil, camphor, eucalyptol, menthol and/or alpha-pinene;
- Balsamic ingredients: coumarine, ethylvanillin and/or vanillin;
- Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;
- Floral ingredients: Methyl dihydrojasmonate, linalool, Citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixture of methyl-ionones isomers;
- Fruity ingredients: gamma ungamma-dodecalactoneactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;
- Green ingredients: 2,4-Dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;
- Musk ingredients: 1,4-dioxa-5,17-cycloheptadecane-dione, pentadecenolide, 3-Methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

Perfuming co-ingredients may not be limited to the above mentioned, and many other of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that the co-ingredients may also be compounds known to release in a controlled manner various types of perfuming compounds.

By "perfumery adjuvant" what is meant is an ingredient capable of imparting additional added benefit such as a color, a particular light resistance, chemical stability, etc.

A detailed description of the nature and type of adjuvant commonly used in perfumery cannot be exhaustive, but it has to be mentioned that the ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), color agents (e.g. dyes and/or pigments), preservative (e.g. antibacterial or antimicrobial or antifungi or anti irritant agents), abrasives, skin cooling agents, fixatives, insect repellants, ointments, vitamins and mixture thereof.

It is understood that a person skilled in the art is perfectly able to design optimal formulations for the desired effect by admixing the above mentioned components of a perfuming composition, simply by applying the standard knowledge of the art as well as by trial and error methodologies.

A perfuming composition consisting of at least one antimicrobial composition as defined above and at least one perfumery carrier represents a particular aspect of the disclosure as well as a perfuming composition comprising at least one antimicrobial composition as defined above, at least one perfumery carrier, at least one perfumery co-ingredient, and optionally at least one perfumery adjuvant.

For the sake of clarity, it is also understood that any mixture resulting directly from a chemical synthesis, e.g. a reaction medium without an adequate purification, in which the compound of the present disclosure would be involved as a starting, intermediate or end-product could not be considered as a perfuming composition according to the disclosure as far as the mixture does not provide the inventive compound in a suitable form for perfumery. Thus, unpurified reaction mixtures are generally excluded from the present disclosure unless otherwise specified.

Furthermore, the antimicrobial composition, as defined above, can also be advantageously used in all the fields of modern perfumery, i.e. fine or functional perfumery, to positively impart or modify the odor of a consumer product into which the compound (I) is added. Consequently, another object of the present disclosure is represented by a perfuming consumer product comprising, at least one antimicrobial composition comprising nona-2,6-dien-1-ol and a least a compound selected from the group consisting of 3-neopentylpyridine, 2-methylhexan-3-one oxime, terpineol and 2-isopropyl-5-methylphenol. Alternatively, the perfuming consumer product comprises at least one antimicrobial composition comprising nona-2,6-dien-1-ol and a least a compound selected from the group consisting of 3-neopentylpyridine and 2-methylhexan-3-one oxime.

The above-composition can be added as such or as part of the present disclosure's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface) or in the air. In other words, a perfuming consumer product according to the disclosure is a perfumed consumer product which comprises the functional formulation, as well as optionally additional benefit agents, corresponding to the desired consumer product, e.g. a detergent or an air freshener, and an olfactive effective amount of at least one disclosure's compound. For the sake of clarity, the perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of the product.

Non-limiting examples of suitable perfuming consumer product can be a perfume, such as a fine perfume, a splash or eau de perfume, a cologne or a shave or after-shave lotion; a fabric care product, such as a liquid or solid detergent, a fabric softener, a fabric refresher, an ironing water, a paper, or a bleach, carpet cleaners, curtain-care products; a body-care product, such as a hair care product (e.g. a shampoo, a coloring preparation or a hair spray, a color care product, hair shaping product, a dental care product), a disinfectant, an intimate care product; a cosmetic preparation (e.g. a skin cream or lotion, a vanishing cream or a deodorant or antiperspirant (e.g. a spray or roll on), hair remover, tanning or sun or after sun product, nail products, skin cleansing, a makeup); or a skin-care product (e.g. a perfumed soap, shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, furnisher care, wipe, a dish detergent or hard-surface (e.g. a floor, bath, sanitary or a windows) detergent; a leather care product; a car care product, such as a polish, waxes or a plastic cleaners. Alternatively, in some aspects, the consumer products are body care or home care products.

Some of the above-mentioned perfuming consumer products may represent an aggressive medium for the disclosure's composition, so that it may be necessary to protect the latter from premature decomposition, for example by encapsulation or by chemically binding it to another chemical which is suitable to release the disclosure's ingredient upon a suitable external stimulus, such as an enzyme, light, heat or a change of pH.

The proportions in which the composition according to the disclosure can be incorporated into the various aforementioned products or compositions vary within a wide range of values. These values are dependent on the nature of the article to be perfumed and on the desired organoleptic effect as well as on the nature of the co-ingredients when the compounds according to the disclosure are mixed with perfuming co-ingredients, solvents or additives commonly used in the art.

For example, in the case of perfuming compositions, typical concentrations are in the order of 0.001% to 10% by weight, or even more, of the disclosure's composition based on the weight of the composition into which they are incorporated. Concentrations lower than these, such as in the order of 0.01% to 1% by weight, can be used when these compounds are incorporated into perfuming consumer products, percentage being relative to the weight of the article.

In some aspects, the present disclosure provides the use or a method of using a composition comprising nona-2,6-dien-1-ol and at least one compound selected from the group consisting of 3-neopentylpyridine, 2-methylhexan-3-one oxime, terpineol and 2-isopropyl-5-methylphenol, wherein the composition is present in an amount sufficient to provide an antimicrobial effect, for the preparation of an antimicrobially active consumer product.

In some aspects, the present disclosure provides the use or a method of using a composition comprising gamma-dodecalactone in combination with at least one ingredient selected from the group consisting of 1-Methyl-4-(1-methylethenyl)-cyclohexene, 4-Methoxybenzaldehyde, and 1,3-Benzodioxole-5-carbaldehyde, wherein the composition is present in an amount sufficient to provide an antimicrobial effect, for the preparation of an antimicrobially active consumer product.

In some aspects, the present disclosure provides the use or a method of using a composition comprising 1,3-Benzodioxole-5-carbaldehyde and gamma-dodecalactone, wherein the composition is present in an amount sufficient to provide an antimicrobial effect, for the preparation of an antimicrobially active consumer product.

In some aspects, the present disclosure provides the use or a method of using a composition comprising 1,3-Benzodioxole-5-carbaldehyde and 4-Methoxybenzaldehyde, wherein the composition is present in an amount sufficient to provide an antimicrobial effect, for the preparation of an antimicrobially active consumer product.

In some aspects, the present disclosure provides the use or a method of using a composition comprising a composition comprising 1,3-Benzodioxole-5-carbaldehyde and 4-Methoxybenzaldehyde, wherein the composition is present in an amount sufficient to provide an antimicrobial effect, for the preparation of an antimicrobially active consumer product.

By the expression "antimicrobially active consumer product" it is meant the normal meaning in the art: i.e. a consumer product which is expected to inhibit the growth of microorganism or to kill the microorganism present on the surface to which it is applied (e.g. skin, hair, textile, or home surface).

The disclosure also provides particular methods of use including counteracting microbial activity in a perfuming or consumer product in particular by circumventing the presence of chlorinated biocides in such products. These methods comprise adding to or incorporating in such products a composition selected from the group consisting of: (i) a composition comprising at least nona-2,6-dien-1-ol in combination with at least one ingredient selected from the group consisting of 3-neopentylpyridine, 2-methylhexan-3-one oxime, terpineol and 2-isopropyl-5-methylphenol; (ii) a composition comprising at least gamma-dodecalactone in combination with at least one ingredient selected from the group consisting of 1-Methyl-4-(1-methylethenyl)-cyclohexene, 4-Methoxybenzaldehyde, and 1,3-Benzodioxole-5-carbaldehyde; (iii) a composition comprising at least 1,3-Benzodioxole-5-carbaldehyde and gamma-dodecalactone; (iv) a composition comprising at least 1,3-Benzodioxole-5-carbaldehyde and 4-Methoxybenzaldehyde; and (v) a composition comprising at least 1,3-Benzodioxole-5-carbaldehyde and 4-Methoxybenzaldehyde, wherein the composition provides an antimicrobial effect. Thus, the use of chlorinated biocides can be avoided or eliminated.

EXAMPLES

The disclosure will now be described in further detail by way of the following examples, wherein the abbreviations have the usual meaning in the art and the temperatures are indicated in degrees centigrade (° C.).

Example 1

Measurement of the Antimicrobial Activity of a Composition According to the Present Disclosure Method to Assess Antimicrobial Activity The method below allows evaluating antimicrobial activity of different raw materials in combination. The Fractional Inhibitory Concentration Index (FIC Index) is a measure of activity (Garcia L. S., Clinical Microbiology Procedures Handbook, pg. 140-162, 3rd Edition (2010), ASM Press, Washington DC) and is calculated according to the formula below:

$$\sum FIC\ \text{Index} = \frac{MIC_A\text{combination}}{MIC_A\text{alone}} + \frac{MIC_B\text{combination}}{MIC_B\text{alone}}$$

where ($MIC_A$ alone) and ($MIC_B$ alone) are the Minimal Inhibitory Concentrations (MIC) of individual ingredients A and B when used in isolation, respectively; whereas ($MIC_A$ combination) and ($MIC_B$ combination) are the Minimal Inhibitory Concentrations of materials A and B when tested in combination. Ingredient A corresponds to nona-2,6-dien-1-ol and ingredient B stands for 3-neopentylpyridine, 2-methylhexan-3-one oxime, terpineol or 2-isopropyl-5-methylphenol.

The Minimal Inhibitory Concentration of a material is defined as the lowest concentration of an agent which can inhibit visible bacterial growth (CLSI M08-A8 Methods for dilution Antimicrobial Susceptibility Test for Bacteria That Grow Aerobically; Approved Standard-Eighth Edition).

A combination of raw materials is considered to exert a partially synergistic antimicrobial effect (or also called antimicrobial additive effect) if the FIC Index is inferior to 1 and a synergistic antimicrobial effect if the FIC Index is inferior or equal to 0.5. FIC Index values inferior or equal to 4 but superior or equal to 1 indicate indifference, whereas FIC index values superior to 4 indicate antagonism (Garcia L. S., Clinical Microbiology Procedures Handbook, pg. 140-162, 3rd Edition (2010), ASM Press, Washington DC).

Preparation of Bacteria Material

Bacterial suspensions of *E. coli* DSMZ 1103 and *S. aureus* DSMZ 1104 were prepared as follows: a frozen stock aliquot was streaked on a Tryptic Soy Agar plate, which was then incubated at 37° C. for 24 hours. A single bacterial colony was picked and inoculated into 50 ml of Mueller Hinton Broth contained in a 100 ml-flask. Incubation was performed overnight at 37° C., under agitation (160 rpm). The following day, the overnight culture was diluted into 50 ml of fresh Mueller Hinton Broth at 1:50 and 1:100 for *S. aureus* and *E. coli*, respectively. Growth at 37° C. was continued as described above until the absorbance measured at 600 nm reached 0.7-0.9 and 0.3-0.45 for *S. aureus* and *E. coli*, respectively. At this point, cells were harvested by centrifugation (10 min-5000×g-4° C.) and suspended in fresh Mueller Hinton Broth at a concentration of $1\times10^8$ CFU/ml.

Measurement of Antimicrobial Effect

Solutions of raw materials under evaluation (ingredients A and B) were prepared in ethanol and then serially diluted in the desired concentration into 96-well microtiter plates (10 µl per well). Columns 1, 10, 11 and 12 received only 10 µl ethanol without any testing material. The final concentration of ethanol was 5% w/v for all wells.

Then, 90 µl of cell suspension as prepared above were added to each well of the microtiter plate, with the exception of column 12 which received 90 µl of Mueller Hinton Broth. The final volume of each well was brought to 200 µl with Mueller Hinton Broth. Each plate was sealed and incubated at 37° C. for 24 hours, under agitation (160 rpm). After incubation, plate reading was performed visually by recording wells with visible bacterial growth. Each combination of materials was tested in triplicate. Turbidity due to potential precipitation of raw materials was taken into account by scoring plates containing identical raw material concentrations, without bacteria.

Results

Based on the test described above, the following combinations of raw materials were found to be antimicrobially active on *E. coli* DSMZ 1103:

TABLE 1

FIC of a composition comprising (2E,6Z)-nona-2,6-dien-1-ol as ingredient A and 2-isopropyl-5-methylphenol as ingredient B.

| Concentration (ppm) | | |
|---|---|---|
| Ingredient A | Ingredient B | FIC |
| 600 | 0 | 1.000 |
| 300 | 150 | 0.750 |
| 150 | 150 | 0.500 |
| 75 | 300 | 0.625 |
| 0 | 600 | 1.000 |

TABLE 2

FIC of a composition comprising (2E,6Z)-nona-2,6-dien-1-ol as ingredient A and 2-isopropyl-5-methylphenol as ingredient B.

| Concentration (ppm) | | |
|---|---|---|
| Ingredient A | Ingredient B | FIC |
| 800 | 0 | 1.000 |
| 400 | 25 | 0.563 |
| 400 | 50 | 0.625 |
| 200 | 100 | 0.500 |
| 100 | 200 | 0.625 |
| 50 | 400 | 0.563 |
| 25 | 400 | 0.531 |
| 0 | 800 | 1.000 |

TABLE 3

FIC of a composition comprising (2E,6Z)-nona-2,6-dien-1-ol as ingredient A and 3-neopentylpyridine as ingredient B.

| Concentration (ppm) | | |
|---|---|---|
| Ingredient A | Ingredient B | FIC |
| 300 | 0 | 1.000 |
| 150 | 75 | 0.625 |
| 75 | 75 | 0.375 |
| 75 | 150 | 0.500 |
| 75 | 300 | 0.750 |
| 0 | 600 | 1.000 |

TABLE 4

FIC of a composition comprising (2E,6Z)-nona-2,6-dien-1-ol as ingredient A and 3-neopentylpyridine as ingredient B.

| Concentration (ppm) | | |
|---|---|---|
| Ingredient A | Ingredient B | FIC |
| 800 | 0 | 1.000 |
| 400 | 25 | 0.531 |
| 400 | 50 | 0.563 |
| 400 | 100 | 0.625 |
| 400 | 200 | 0.750 |
| 200 | 400 | 0.750 |
| 100 | 400 | 0.625 |
| 50 | 800 | 1.063 |
| 25 | 800 | 1.031 |
| 0 | 800 | 1.000 |

TABLE 5

FIC of a composition comprising gamma-dodecalactone as ingredient A and 1,3-Benzodioxole-5-carbaldehyde as ingredient B.

| Concentration (ppm) | | |
|---|---|---|
| Ingredient A | Ingredient B | FIC |
| 2400 | 0 | 1.000 |
| 1200 | 300 | 0.750 |
| 600 | 300 | 0.500 |
| 300 | 600 | 0.625 |
| 150 | 600 | 0.563 |
| 75 | 600 | 0.531 |
| 0 | 1200 | 1.000 |

TABLE 6

FIC of a composition comprising gamma-dodecalactone as ingredient A and 4-Methoxybenzaldehyde as ingredient B.

| Concentration (ppm) | | |
|---|---|---|
| Ingredient A | Ingredient B | FIC |
| 1200 | 0 | 1.000 |
| 600 | 150 | 0.625 |
| 300 | 150 | 0.375 |
| 150 | 300 | 0.375 |
| 150 | 600 | 0.625 |
| 0 | 1200 | 1.000 |

TABLE 7

FIC of a composition comprising (Z)-3,7-Dimethyl-2,6-octadien-1-ol as ingredient A and gamma-dodecalactone as ingredient B.

| Concentration (ppm) | | |
|---|---|---|
| Ingredient A | Ingredient B | FIC |
| 1200 | 0 | 1.000 |
| 600 | 75 | 0.563 |
| 600 | 150 | 0.625 |
| 300 | 300 | 0.500 |
| 150 | 300 | 0.375 |
| 150 | 600 | 0.625 |
| 0 | 1200 | 1.000 |

TABLE 8

FIC of a composition comprising cis-4(Isopropyl)cyclohexanemethanol as ingredient A and 4-Methoxybenzaldehyde as ingredient B.

| Concentration (ppm) | | |
|---|---|---|
| Ingredient A | Ingredient B | FIC |
| 9600 | 0 | 1.000 |
| 4800 | 150 | 0.625 |
| 2400 | 150 | 0.375 |
| 1200 | 150 | 0.250 |
| 600 | 150 | 0.188 |
| 600 | 300 | 0.313 |
| 300 | 600 | 0.531 |
| 150 | 600 | 0.516 |
| 0 | 1200 | 1.000 |

Based on the test described above, the following combinations of raw materials were found to be antimicrobially active on *S. aureus* DSMZ 1104:

TABLE 9

FIC of a composition comprising (2E,6Z)-nona-2,6-dien-1-ol as ingredient A and 3-neopentylpyridine as ingredient B.

| Concentration (ppm) | | |
|---|---|---|
| Ingredient A | Ingredient B | FIC |
| 600 | 0 | 1.00 |
| 300 | 75 | 0.75 |
| 150 | 75 | 0.50 |
| 75 | 75 | 0.38 |
| 75 | 150 | 0.63 |
| 0 | 300 | 1.00 |

TABLE 10

FIC of a composition comprising (2E,6Z)-nona-2,6-dien-1-ol as ingredient A and 3-neopentylpyridine as ingredient B.

| Concentration (ppm) | | |
|---|---|---|
| Ingredient A | Ingredient B | FIC |
| 800 | 0 | 1.00 |
| 800 | 25 | 1.02 |
| 800 | 50 | 1.03 |
| 800 | 100 | 1.06 |
| 800 | 200 | 1.13 |
| 400 | 400 | 0.75 |
| 200 | 800 | 0.75 |

TABLE 10-continued

FIC of a composition comprising (2E,6Z)-nona-2,6-dien-1-ol as ingredient A and 3-neopentylpyridine as ingredient B.

| Concentration (ppm) | | |
|---|---|---|
| Ingredient A | Ingredient B | FIC |
| 100 | 800 | 0.63 |
| 50 | 1600 | 1.06 |
| 25 | 1600 | 1.03 |
| 0 | 1600 | 1.00 |

TABLE 11

FIC of a composition comprising (2E,6Z)-nona-2,6-dien-1-ol as ingredient A and 2-methylhexan-3-one oxime as ingredient B.

| Concentration (ppm) | | |
|---|---|---|
| Ingredient A | Ingredient B | FIC |
| 1200 | 0 | 1.00 |
| 600 | 150 | 0.531 |
| 600 | 300 | 0.563 |
| 600 | 600 | 0.625 |
| 300 | 1200 | 0.500 |
| 150 | 2400 | 0.625 |
| 75 | 2400 | 0.563 |
| 0 | 4800 | 1.00 |

TABLE 12

FIC of a composition comprising (2E,6Z)-nona-2,6-dien-1-ol as ingredient A and 2-methylhexan-3-one oxime as ingredient B.

| Concentration (ppm) | | |
|---|---|---|
| Ingredient A | Ingredient B | FIC |
| 800 | 0 | 1.000 |
| 800 | 50 | 1.016 |
| 800 | 100 | 1.031 |
| 800 | 200 | 1.063 |
| 800 | 400 | 1.125 |
| 800 | 800 | 1.250 |
| 400 | 1600 | 1.000 |
| 200 | 1600 | 0.750 |
| 100 | 1600 | 0.625 |
| 50 | 3200 | 1.063 |
| 25 | 3200 | 1.031 |
| 0 | 3200 | 1.00 |

TABLE 13

FIC of a composition comprising (2E,6Z)-nona-2,6-dien-1-ol as ingredient A and α-terpineol as ingredient B.

| Concentration (ppm) | | |
|---|---|---|
| Ingredient A | Ingredient B | FIC |
| 2400 | 0 | 1.00 |
| 1200 | 75 | 0.56 |
| 1200 | 150 | 0.63 |
| 600 | 300 | 0.50 |
| 300 | 600 | 0.63 |
| 0 | 1200 | 1.00 |

TABLE 14

| FIC of a composition comprising (2E,6Z)-nona-2,6-dien-1-ol as ingredient A and α-terpineol as ingredient B. | | |
|---|---|---|
| Concentration (ppm) | | |
| Ingredient A | Ingredient B | FIC |
| 800 | 0 | 1.00 |
| 800 | 25 | 1.02 |
| 800 | 50 | 1.03 |
| 800 | 100 | 1.06 |
| 800 | 200 | 1.13 |
| 800 | 400 | 1.25 |
| 400 | 800 | 1.00 |
| 200 | 800 | 0.75 |
| 100 | 1600 | 1.13 |
| 50 | 1600 | 1.06 |
| 25 | 1600 | 1.03 |
| 0 | 1600 | 4.00 |

TABLE 15

| FIC of a composition comprising gamma-dodecalactone as ingredient A and 4-Methoxybenzaldehyde as ingredient B. | | |
|---|---|---|
| Concentration (ppm) | | |
| Ingredient A | Ingredient B | FIC |
| 1200 | 0 | 1.00 |
| 600 | 150 | 0.52 |
| 600 | 300 | 0.53 |
| 600 | 600 | 0.56 |
| 300 | 1200 | 0.38 |
| 300 | 2400 | 0.50 |
| 150 | 4800 | 0.63 |
| 75 | 4800 | 0.56 |
| 0 | 9600 | 1.00 |

TABLE 16

| FIC of a composition comprising 1,3-Benzodioxole-5-carbaldehyde as ingredient A and 4-Methoxybenzaldehyde as ingredient B. | | |
|---|---|---|
| Concentration (ppm) | | |
| Ingredient A | Ingredient B | FIC |
| 1200 | 0 | 1.00 |
| 600 | 75 | 0.56 |
| 300 | 150 | 0.38 |
| 150 | 150 | 0.25 |
| 75 | 300 | 0.31 |
| 75 | 600 | 0.56 |
| 0 | 1200 | 1.00 |

Those tables demonstrate that the above compositions present an antimicrobial synergistic effect as the FIC of those compositions are below or equal to 1.

Example 2

Antibacterial Effect of Compositions According to Some Aspects Presented Herein in a Liquid Soap Base Preparation of Bacterial Solutions Bacterial solutions of the two strains, *E. coli* DSMZ 1103 and *S. aureus* DSMZ 1104, were prepared for BCT test as follows. Stock cultures stored at −80° C. were sub-cultured onto Tryptic Soy Agar (TSA) agar plate media, and incubated at 37° C. for 24 h to obtain single colonies. Single colonies of the primary cultures were streaked onto TSA slant and incubate it at 37° C. incubator for 24 h. Bacterial lawns of the slant culture were collected in PBS buffer to make suspensions with the target level of 1-5×$10^8$ CFU/mL. The 1:100 dilution of each cell suspension in PBS buffer was used as the bacterial solutions for the BCT test.

Preparation of Test Samples

Test samples of base with synergistic binary mixtures were prepared as follows. Raw materials of the synergistic binary mixtures (Table 17) were mixed with the liquid soap base PGK-10-003 (Table 18). Aliquots (2.5 g) of each mixture were weighed into 20 ml glass tube with a stirrer bar, and added with equal amount of MilliQ water to make 50% suspension as the test samples for the BCT test.

TABLE 17

| Compositions tested. | |
|---|---|
| Tested against *E. coli* DSMZ 1103 | Tested against *S. aureus* DSMZ 1104 |
| 0.5% (2E,6Z)-nona-2,6-dien-1-ol + 0.5% 2-isopropyl-5-methylphenol | 0.4% (2E,6Z)-nona-2,6-dien-1-ol + 0.2% 2-isopropyl-5-methylphenol |
| 0.6% (2E,6Z)-nona-2,6-dien-1-ol + 0.6% 2-isopropyl-5-methylphenol | 0.6% (2E,6Z)-nona-2,6-dien-1-ol + 0.3% 2-isopropyl-5-methylphenol |
| 0.5% (2E,6Z)-nona-2,6-dien-1-ol + 0.5% 3-neopentylpyridine | 0.18% (2E,6Z)-nona-2,6-dien-1-ol + 0.72% 2-methylhexan-3-one oxime |
| 0.6% (2E,6Z)-nona-2,6-dien-1-ol + 0.6% 3-neopentylpyridine | 0.3% (2E,6Z)-nona-2,6-dien-1-ol + 1.2% 2-methylhexan-3-one oxime |
| | 0.36% (2E,6Z)-nona-2,6-dien-1-ol + 0.36% 3-neopentylpyridine |

TABLE 18

| Liquid soap base | |
|---|---|
| Composition | % |
| Water | 60.1 |
| Sodium benzoate | 0.5 |
| Sodium laureth sulfate | 24.0 |
| Coco glucoside | 4.0 |
| PEG-7 glyceryl cocoate | 2.0 |
| Coco-betaine | 6.0 |
| Sodium chloride | 2.0 |
| Citric acid (50%) | 0.4 |
| PEG-40 Hydrogenated castor oil | 0.5 |

BCT Test

BCT tests were performed in the 20 ml sample tubes. Each sample tube with 5 g of 50% sample suspension was placed onto a magnetic stirrer, and an aliquot of bacterial solution (100 μl) was added to the sample and allowed for a contact of 45 sec during mixing. Then aliquots (0.5 ml) of the mixture were transferred into 5 ml PBS, and further serial dilutions were made in 4.5 ml PBS. Aliquots (0.5 ml) of PBS dilutions were plated onto duplicate plates of TSA plates using the pour plate method. TSA plates were incubated at 37° C. for 48 h. After incubation, colonies on TSA plates were enumerated and log reduction of each sample were calculated against the CFU counts of the control sample (MilliQ water).

Table 19 indicates that binary mixtures of (2E,6Z)-nona-2,6-dien-1-ol: 2-isopropyl-5-methylphenol (1:1) at 0.5% and 0.6% and (2E,6Z)-nona-2,6-dien-1-ol: 3-neopentylpyridine (1:1) at 0.5% and 0.6% had 1.1, 1.8, 0.6, and 1.4 log reduction against *E. coli* DSMZ 1103, respectively, in 50% liquid soap base after a contact time of 45 sec.

TABLE 19

| Antibacterial efficacy of compositions according to some aspects presented herein against *E. coli* DSMZ 1103 in 50% liquid soap base | |
|---|---|
| Composition of binary mixtures | Average log reduction ± SEM (n = 3) |
| Without mixture | 0.3 ± 0.3 |
| 0.25% (2E,6Z)-nona-2,6-dien-1-ol + 0.25% 2-isopropyl-5-methylphenol | 1.1 ± 0.2 |
| 0.3% (2E,6Z)-nona-2,6-dien-1-ol + 0.3% 2-isopropyl-5-methylphenol | 1.8 ± 0.2 |
| 0.25% (2E,6Z)-nona-2,6-dien-1-ol + 0.25% 3-neopentylpyridine | 0.6 ± 0.1 |
| 0.3% (2E,6Z)-nona-2,6-dien-1-ol + 0.3% 3-neopentylpyridine | 1.4 ± 0.1 |

Table 20 shows that binary mixtures of (2E,6Z)-nona-2,6-dien-1-ol: 2-isopropyl-5-methylphenol (2:1) at 0.3% and 0.45%, (2E,6Z)-nona-2,6-dien-1-ol: 2-methylhexan-3-one oxime (1:4) at 0.45% and 0.75%, and (2E,6Z)-nona-2,6-dien-1-ol: 3-neopentylpyridine (1:1) at 0.36% had 1.4 to 3.2 log reduction against *S. aureus* DSMZ 1104 in 50% liquid soap base after a contact time of 45 sec.

TABLE 20

| Antibacterial efficacy of compositions according to some aspects presented herein against *S. aureus* DSMZ 1104 in 50% liquid soap base | |
|---|---|
| Composition of binary mixtures | Average log reduction ± SEM (n = 3) |
| Without mixture | 0.6 ± 0.2 |
| 0.2% (2E,6Z)-nona-2,6-dien-1-ol + 0.1% 2-isopropyl-5-methylphenol | 1.4 ± 0.4 |
| 0.3% (2E,6Z)-nona-2,6-dien-1-ol + 0.15% 2-isopropyl-5-methylphenol | 2.2 ± 0.5 |
| 0.09% (2E,6Z)-nona-2,6-dien-1-ol + 0.36% 2-methylhexan-3-one oxime | 2.6 ± 0.2 |
| 0.15% (2E,6Z)-nona-2,6-dien-1-ol + 0.6% 2-methylhexan-3-one oxime | 3.2 ± 0.1 |
| 0.18% (2E,6Z)-nona-2,6-dien-1-ol + 0.18% 3-neopentylpyridine | 1.9 ± 0.2 |

In conclusion, the data indicates that synergistic binary mixtures shows antibacterial effect against both *E. coli* DSMZ 1103 and *S. aureus* DSMZ 1104 in a liquid soap base.

Table 21 showed that the measured bacterial log reduction observed using of mixtures of 0.3% (2E,6Z)-nona-2,6-dien-1-ol+0.3% 3-neopentylpyridine is greater than the sum of the measured bacterial log reduction observed either 0.3% (2E,6Z)-nona-2,6-dien-1-ol or 0.3% 3-neopentylpyridine in isolation. Similarly, the log reduction of mixtures of 0.3% (2E,6Z)-nona-2,6-dien-1-ol+0.3% 2-isopropyl-5-methylphenol is greater than that of 0.3% (2E,6Z)-nona-2,6-dien-1-ol or 0.3% 2-isopropyl-5-methylphenol.

TABLE 21

| Comparison of the antibacterial efficacy of synergistic binary mixture with that o fsingle materials against *E. coli* DSMZ 1103 in 50% liquid soap base | |
|---|---|
| Composition of binary mixtures | Average log reduction ± SEM (n = 2) |
| Without mixture | 0.0 ± 0.0 |
| 0.3% (2E,6Z)-nona-2,6-dien-1-ol + 0.3% 3-neopentylpyridine | 1.4 ± 0.1 |

TABLE 21-continued

| Comparison of the antibacterial efficacy of synergistic binary mixture with that o fsingle materials against *E. coli* DSMZ 1103 in 50% liquid soap base | |
|---|---|
| Composition of binary mixtures | Average log reduction ± SEM (n = 2) |
| 0.3% (2E,6Z)-nona-2,6-dien-1-ol + 0.3% 2-isopropyl-5-methylphenol | 1.8 ± 0.2 |
| 0.3% (2E,6Z)-nona-2,6-dien-1-ol | 0.3 ± 0.2 |
| 0.3% 3-neopentylpyridine | 0.3 ± 0.2 |
| 0.3% 2-isopropyl-5-methylphenol | 0.4 ± 0.0 |

Example 3

Antibacterial Effect of Compositions According to Some Aspects Presented Herein in a Roll-on Deodorant Base

Preparation of Bacterial Solutions

Bacterial solution of *C. xerosis* ATCC 373 strain was prepared for BCT test as follows. Stock cultures stored at −80° C. were subcultured onto Tryptic Soy Agar media with 0.5% Tween 80 (TSA-TW80), and incubated at 37° C. for 48 h. The primary cultures were subcultured onto TSA-TW80 again to prepare the secondary cultures. Single colonies of secondary culture were inoculated into 30 ml of Brain Heart Infusion (BHI) broth with 0.5% Tween 80 (BHI-TW80), and incubated at 37° C. 180 rpm for 24 h. Aliquots (1 ml) of the 24 h culture were inoculated into 30 ml of fresh BHI-TW80 broth, and incubated at 37° C. 180 rpm for 48 h. Aliquots (2-3 ml) of the 48 h culture were inoculated into four 50 ml of fresh BHI-TW80 broth medium, and incubated at 37° C. 180 rpm for 4-6 hrs. When the OD reached the target value of 1.6, cells were harvested by centrifugation at 5000 rpm for 10 min, and then resuspended in the same fresh broth media to a target concentration of $10^9$ to $10^{10}$ cfu/mL. This suspension was used as the bacterial solution for the BCT test.

Preparation of Test Samples

Test samples of base with synergistic binary mixtures were prepared as follows. Raw materials of the synergistic binary mixtures were weighed (Table 22), and mixed with 0.3 g PEG-40 Hydrogenated Castor Oil and 9.57 g deodorant roll on base (Table 23).

TABLE 22

| Compositions tested. | |
|---|---|
| Weight of raw materials | % in test sample |
| (2E,6Z)-nona-2,6-dien-1-ol 40 mg + 2-isopropyl-5-methylphenol 20 mg | 0.4% (2E,6Z)-nona-2,6-dien-1-ol + 0.2% 2-isopropyl-5-methylphenol |
| (2E,6Z)-nona-2,6-dien-1-ol 24 mg + 2-isopropyl-5-methylphenol 24 mg | 0.24% (2E,6Z)-nona-2,6-dien-1-ol + 0.24% 2-isopropyl-5-methylphenol |
| (2E,6Z)-nona-2,6-dien-1-ol 12 mg + 2-methylhexan-3-one oxime 12 mg | 0.12% (2E,6Z)-nona-2,6-dien-1-ol + 0.48% 2-methylhexan-3-one oxime |
| (2E,6Z)-nona-2,6-dien-1-ol 20 mg + Terpineol 40 mg | 0.2% (2E,6Z)-nona-2,6-dien-1-ol + 0.4% Terpineol |
| (2E,6Z)-nona-2,6-dien-1-ol 24 mg + 3-neopentylpyridine 24 mg | 0.24% (2E,6Z)-nona-2,6-dien-1-ol + 0.24% 3-neopentylpyridine |

TABLE 23

| Roll-on deodorant soap base | |
|---|---|
| Composition | % |
| Water deionised | 50 |
| 2 NATROSOL 250 H Hydroxyethylcellulose | 0.7 |
| Ethyl alcohol 95° | 40 |
| 1,2-Propylene glycol | 5 |

BCT Test

BCT tests were performed in 15 ml sample tubes. Aliquots (0.9 g) of each sample were weighed into the tube, and an aliquot of bacterial solution (100 μl) was added to the sample and allowed for a contact time of 120 sec with constant mixing. At the end of the contact time, aliquots (9 ml) of BHI broth were added to the tube. The suspensions were mixed well by vortexing, and further 1:10 serial dilutions were made in 9.9 ml BHI. Aliquots (1 ml) of BHI dilutions were plated onto duplicate plates of TSA-TW80 using pour plate methods. TSA-TW80 plates were incubated at 37° C. for 2-3 days. After incubation, colonies on TSA-TW80 plates were enumerated and log reduction of each sample were calculated against the CFU counts of the control sample (BHI).

Table 24 indicates that the addition of binary mixtures of (2E,6Z)-nona-2,6-dien-1-ol: 2-isopropyl-5-methylphenol (1:2) at 0.54%, (2E,6Z)-nona-2,6-dien-1-ol: 2-isopropyl-5-methylphenol (1:1) at 0.432%, (2E,6Z)-nona-2,6-dien-1-ol: 2-methylhexan-3-one oxime (1:4) at 0.54%, (2E,6Z)-nona-2,6-dien-1-ol: Terpineol (1:4) at 0.54%, (2E,6Z)-nona-2,6-dien-1-ol: 3-neopentylpyridine (1:1) at 0.432% in the 90% deodorant roll-on base improve the antimicrobial effect of base against *C. xerosis* ATCC 373 after a contact time of 120 sec.

TABLE 24

Antibacterial efficacy of synergistic binary mixtures against *C. xerosis* ATCC 373 in 90% roll-on deodorant base

| Composition of binary mixtures | Average log reduction ± SEM (n ± 2) |
|---|---|
| Without mixture | 5.4 ± 0.0 |
| 0.36% (2E,6Z)-nona-2,6-dien-1-ol + 0.18% 2-isopropyl-5-methylphenol | 6.6 ± 0.2 |
| 0.216% (2E,6Z)-nona-2,6-dien-1-ol + 0.216% 2-isopropyl-5-methylphenol | 6.3 ± 0.2 |
| 0.108% (2E,6Z)-nona-2,6-dien-1-ol + 0.432% 2-methylhexan-3-one oxime | 6.1 ± 0.2 |
| 0.18% (2E,6Z)-nona-2,6-dien-1-ol + 0.36% Terpineol | 6.4 ± 0.3 |
| 0.216% (2E,6Z)-nona-2,6-dien-1-ol + 0.216% 3-neopentylpyridine | 5.8 ± 0.2 |

Table 25 shows that mixture of (0.216% (2E,6Z)-nona-2,6-dien-1-ol+0.216% 2-isopropyl-5-methylphenol) had greater log reduction than that of 0.216% (2E,6Z)-nona-2,6-dien-1-ol or 0.216% 2-isopropyl-5-methylphenol. However, a mixture of (0.216% (2E,6Z)-nona-2,6-dien-1-ol+0.216% 3-neopentylpyridine) had similar log reduction as that of 0.216% (2E,6Z)-nona-2,6-dien-1-ol or 0.216% 3-neopentylpyridine.

TABLE 25

Comparison of the antibacterial efficacy of synergistic binary mixtures with that of single materials against *C. xerosis* ATCC 373 in 90% roll-on deodorant base

| Composition of binary mixtures | Log reduction |
|---|---|
| Without mixture | 5.5 |
| 0.216% (2E,6Z)-nona-2,6-dien-1-ol + 0.216% 2-isopropyl-5-methylphenol | 6.5 |
| 0.216% (2E,6Z)-nona-2,6-dien-1-ol + 0.216% 3-neopentylpyridine | 5.9 |
| 0.216% (2E,6Z)-nona-2,6-dien-1-ol | 5.7 |
| 0.216% 2-isopropyl-5-methylphenol | 6.0 |
| 0.216% 3-neopentylpyridine | 5.9 |

The invention claimed is:

1. A composition comprising gamma-dodecalactone in an amount between 25 ppm and 2000 ppm, and 1-methyl-4-(1-methylethenyl)-cyclohexene in an amount between 150 ppm and 500 ppm, wherein the ingredients are present in an amount sufficient to provide an antimicrobial effect, wherein the antimicrobial effect is an inhibition of growth of a bacterial strain selected from the group consisting of *Corynebacterium xerosis, Staphylococcus aureus*, and *Escherichia coli.*

2. The composition of claim 1, further comprising:

an ingredient selected from the group consisting of a perfumery carrier, a perfuming co-ingredient and mixtures thereof; and optionally at least one perfumery adjuvant.

3. A consumer product comprising the composition of claim 1, wherein the consumer product is a perfume.

4. The composition of claim 1, further comprising at least one compound selected from the group consisting of 4-methoxybenzaldehyde and 1,3-benzodioxole-5-carbaldehyde.

5. The composition of claim 4, wherein the amount of the 4-methoxybenzaldehyde is from 300 to 600 ppm, and the amount of the 1,3-benzodioxole-5-carbaldehyde is from 300 to 600 ppm.

6. The composition of claim 1, further comprising 1,3-benzodioxole-5-carbaldehyde and 4-methoxybenzaldehyde.

7. The composition of claim 6, wherein the amount of the 1,3-benzodioxole-5-carbaldehyde is from 75 to 300 ppm, and the amount of the 4-methoxybenzaldehyde is from 150 to 300 ppm.

8. The composition of claim 1, comprising the gamma-dodecalactone in an amount between 50 ppm and 500 ppm.

9. The composition of claim 1, comprising the 1-methyl-4-(1-methylethenyl)-cyclohexene in an amount between 300 ppm and 500 ppm.

10. A consumer product comprising the composition of claim 1, wherein the consumer product is a fabric care product.

11. A consumer product comprising the composition of claim 1, wherein the consumer product is a body-care product.

12. A consumer product comprising the composition of claim 1, wherein the consumer product is a cosmetic preparation.

13. A consumer product comprising the composition of claim 1, wherein the consumer product is a skin-care product.

14. A consumer product comprising the composition of claim 1, wherein the consumer product is an air care product.

15. A consumer product comprising the composition of claim 1, wherein the consumer product is a home care product.

* * * * *